US012569358B2

(12) United States Patent　　　　　(10) Patent No.:　US 12,569,358 B2

Rouse et al.　　　　　　　　　　　　　　(45) Date of Patent:　Mar. 10, 2026

(54) PREDICTING USER PREFERENCE WITH AI TO CONTROL A NEW GENERATION OF WEARABLE ASSISTIVE TECHNOLOGIES

(71) Applicant: THE REGENTS OF THE UNIVERSITY OF MICHIGAN, Ann Arbor, MI (US)

(72) Inventors: Elliott J. Rouse, Ann Arbor, MI (US); Ung Hee Lee, Ann Arbor, MI (US); Varun Shetty, Ann Arbor, MI (US)

( * ) Notice: Subject to any disclaimer, the term of this patent is extended or adjusted under 35 U.S.C. 154(b) by 1069 days.

(21) Appl. No.: 17/535,298

(22) Filed: Nov. 24, 2021

(65) Prior Publication Data

US 2022/0160523 A1　　May 26, 2022

Related U.S. Application Data

(60) Provisional application No. 63/118,556, filed on Nov. 25, 2020.

(51) Int. Cl.
　　*A61F 2/70*　　　(2006.01)
　　*A61F 2/66*　　　(2006.01)
　　*G05B 13/02*　　　(2006.01)
(52) U.S. Cl.
　　CPC ............ *A61F 2/70* (2013.01); *G05B 13/0265* (2013.01); *A61F 2002/6614* (2013.01); *A61F 2002/704* (2013.01)
(58) Field of Classification Search
　　CPC ................ A61F 2/70; A61F 2002/6614; A61F 2002/704; A61F 2/66; A61F 2/6607; G05B 13/0265
　　See application file for complete search history.

(56) References Cited

U.S. PATENT DOCUMENTS 11,278,235 B2 *　3/2022　Herr .................... A61B 5/688
2016/0331557 A1 *　11/2016　Tong .................... A61F 2/6607
(Continued)

OTHER PUBLICATIONS

Ye J. et al. "Functional electrical stimulation based on a pelvis support robot for gait rehabilitation of hemiplegic patients after stroke," *Conf Proc IEEE Eng Med Biol Soc.* 2014;2014: 3098-3101.

(Continued)

*Primary Examiner* — Bruce E Snow
(74) *Attorney, Agent, or Firm* — MARSHALL, GERSTEIN & BORUN LLP

(57)　　　　　ABSTRACT

Techniques are provided for using machine learning methods to predict user preferences with respect to robotic assistive prostheses and/or custom tune the robotic assistive prostheses for individual users based on the predicted user preferences. A training biomechanical dataset, including historical biomechanical sensor data for a robotic assistive prosthetic device operating using a plurality of tuning settings at a plurality of speeds, and a training user preference dataset including historical user tuning preference data for the robotic assistive prosthetic device for each respective tuning setting and speed, are generated. A machine learning model is trained using the training biomechanical dataset and the training user preference dataset. The trained machine learning model is applied to new biomechanical sensor data associated with a particular user to predict the user's tuning preferences for the robotic assistive prosthetic device, and the settings of the device are automatically modified based on the predicted tuning preferences.

14 Claims, 8 Drawing Sheets

(56) References Cited

U.S. PATENT DOCUMENTS

2022/0160523 A1* 5/2022 Rouse .................... A61F 2/70
2022/0257389 A1* 8/2022 Herr .................... A61F 2/68

OTHER PUBLICATIONS

Johnson DC et al. "The evolution of gait in childhood and adolescent cerebral palsy." J Pediatr Orthop. 1997;17: 392-396.

Waters RL et al. "Energy cost of walking of amputees: the influence of level of amputation." J Bone Joint Surg Am. 1976;58: 42-46.

Naschitz JE et al. "Why traumatic leg amputees are at increased risk for cardiovascular diseases." QJM. 2008;101: 251-259.

Breakey JW. Body Image: The Lower-Limb Amputee. J Prosthet Orthot. 1997;9: 58.

Rouse EJ, Mooney LM, Martinez-Villalpando EC, Herr HM. Clutchable series-elastic actuator: design of a robotic knee prosthesis for minimum energy consumption. IEEE Int Conf Rehabil Robot. 2013;2013: 6650383.

Zhang J, Fiers P, Witte KA, Jackson RW, Poggensee KL, Atkeson CG, et al. Human-in-the-loop optimization of exoskeleton assistance during walking. Science. 2017;356: 1280-1284.

Mooney LM, Rouse EJ, Herr HM. Autonomous exoskeleton reduces metabolic cost of human walking during load carriage. Journal of NeuroEngineering and Rehabilitation. 2014. p. 80. doi:10.1186/1743-0003-11-80.

Tucker MR, Olivier J, Pagel A, Bleuler H, Bouri M, Lambercy O, et al. Control strategies for active lower extremity prosthetics and orthotics: a review. J Neuroeng Rehabil. 2015;12: 1.

Tyler R. Clites, Max K. Shepherd, Kimberly A. Ingraham, and Elliott J. Rouse. Patient Preference in the Selection of Prosthetic Joint Stiffness. Proc IEEE RAS EMBS Int Conf Biomed Robot Biomechatron. Dec. 2020.

Shepherd MK, Rouse EJ. Comparing preference of ankle-foot stiffness in below-knee amputees and prosthetists. Scientific Reports. 2020. doi:10.1038/s41598-020-72131-2.

Delp SL, Anderson FC, Arnold AS, Loan P, Habib A, John CT, et al. OpenSim: open-source software to create and analyze dynamic simulations of movement. IEEE Trans Biomed Eng. 2007;54: 1940-1950.

Young AJ, Hargrove LJ. A Classification Method for User-Independent Intent Recognition for Transfemoral Amputees Using Powered Lower Limb Prostheses. IEEE Transactions on Neural Systems and Rehabilitation Engineering. 2016. pp. 217-225. doi:10.1109/tnsre.2015.2412461.

Lee UH, Bi J, Patel R, Fouhey D, Rouse, EJ. Image Transformation and CNNs: A Strategy for Encoding Human Locomotor Intent for Autonomous Wearable Robots. Robotics Automation Letters.

R. Waters, J. Perry, D. Antonelli, and H. Hislop, "Energy cost of walking of amputees: the influence of level of amputation," J Bone Joint Surg Am, vol. 58, No. 1, pp. 42-46, 1976.

T. Lenzi, M. Cempini, L. J. Hargrove, and T. A. Kuiken, "Design, development, and validation of a lightweight nonbackdrivable robotic ankle prosthesis," IEEE/ASME Transactions on Mecha-tronics, vol. 24, No. 2, pp. 471-482, 2019.

E. M. Glanzer and P. G. Adamczyk, "Design and validation of a semi-active variable stiffness foot prosthesis," IEEE Transactions on Neural Systems and Rehabilitation Engineering, vol. 26, No. 12, pp. 2351-2359, 2018.

M. K. Shepherd and E. J. Rouse, "The vspa foot: A quasi-passive ankle-foot prosthesis with continuously variable stiffness," IEEE Transactions on Neural Systems and Rehabilitation Engineering, vol. 25, No. 12, pp. 2375-2386, 2017.

D. J. Braun, V. Chalvet, T.-H. Chong, S. S. Apte, and N. Hogan, "Variable stiffness spring actuators for low-energy-cost human augmentation," IEEE Transactions on Robotics, vol. 35, No. 6, pp. 1435-1449, 2019.

H. Tryggvason, F. Starker, C. Lecomte, and F. Jonsdottir, "Variable stiffness prosthetic foot based on rheology properties of shear thickening fluid," Smart Materials and Structures, vol. 29, No. 9, p. 095008, 2020.

J. Zhang, et al., "Human-in-the-loop optimization of exoskeleton assistance during walking," Science, vol. 356, No. 6344, pp. 1280-1284, 2017.

K. A. Ingraham, C. D. Remy, and E. J. Rouse, "User preference of applied torque characteristics for bilateral powered ankle exoskeletons," in 2020 8th IEEE RAS/EMBS International Conference for Biomedical Robotics and Biomechatronics (BioRob). IEEE, 2020, pp. 839-845.

N. Thatte, H. Duan, and H. Geyer, "A sample-efficient black-box optimizer to train policies for human-in-the-loop systems with user preferences," IEEE Robotics and Automation Letters, vol. 2, No. 2, pp. 993-1000, 2017.

M. Tucker, et al., "Preference-based learning for exoskeleton gait optimization," in 2020 IEEE International Conference on Robotics and Automation (ICRA). IEEE, 2020, pp. 2351-2357.

K. Li, et al., "Roial: Region of interest active learning for characterizing exoskeleton gait preference landscapes," arXiv preprint arXiv:2011.04812, 2020.

M. Tucker, et al., "Human preference-based learning for high-dimensional optimization of exoskeleton walking gaits," in 2020 IEEE/RSJ International Conference on Intelligent Robots and Systems (IROS). IEEE, 2020, pp. 3423-3430.

T. R. Clites, M. K. Shepherd, K. A. Ingraham, L. Wontorcik, and E. J. Rouse, "Understanding patient preference in prosthetic ankle stiffness," Journal of neuroengineering and rehabilitation, vol. 18, No. 1, pp. 1-16, 2021.

M. K. Shepherd, A. F. Azocar, M. J. Major, and E. J. Rouse, "Amputee perception of prosthetic ankle stiffness during locomotion," Journal of neuroengineering and rehabilitation, vol. 15, No. 1, pp. 1-10, 2018.

B. Hu, E. Rouse, and L. Hargrove, "Fusion of bilateral lower-limb neuromechanical signals improves prediction of locomotor activities," Frontiers in Robotics and AI, vol. 5, p. 78, 2018.

F. Pedregosa, et al., "Scikit-learn: Machine learning in Python," Journal of Machine Learning Research, vol. 12, pp. 2825-2830, 2011.

A. J. Smola and B. Schölkopf, "A tutorial on support vector regression," Statistics and computing, vol. 14, No. 3, pp. 199-222, 2004.

D. P. Kingma and J. Ba, "Adam: A method for stochastic optimization," arXiv preprint arXiv:1412.6980, 2014.

M. Abadi, et al., "TensorFlow: Large-scale machine learning on heterogeneous systems," 2015, software available from tensorflow. org. [Online]. Available: https://www.tensorflow.org/.

F. Chollet et al. (2015) Keras. [Online]. Available: https://github. com/fchollet/keras.

S. Hochreiter and J. Schmidhuber, "Long short-term memory," Neural computation, vol. 9, No. 8, pp. 1735-1780, 1997.

A. F. Azocar, L. M. Mooney, J.-F. Duval, A. M. Simon, L. J. Hargrove, and E. J. Rouse, "Design and clinical implementation of an open-source bionic leg," Nature biomedical engineering, vol. 4, No. 10, pp. 941-953, 2020.

L. Gabert, S. Hood, M. Tran, M. Cempini, and T. Lenzi, "A compact, lightweight robotic ankle-foot prosthesis: Featuring a powered polycentric design," IEEE robotics & automation magazine, vol. 27, No. 1, pp. 87-102, 2020.

A. J. Young and D. P. Ferris, "State of the art and future directions for lower limb robotic exoskeletons," IEEE Transactions on Neural Systems and Rehabilitation Engineering, vol. 25, No. 2, pp. 171-182, 2016.

Boonstra et al., "Walking speed of normal subjects and amputees: aspects of validity of gait analysis," Prosthetics and Orthotics International, vol. 17, No. 2, pp. 78-82, 1993.

* cited by examiner

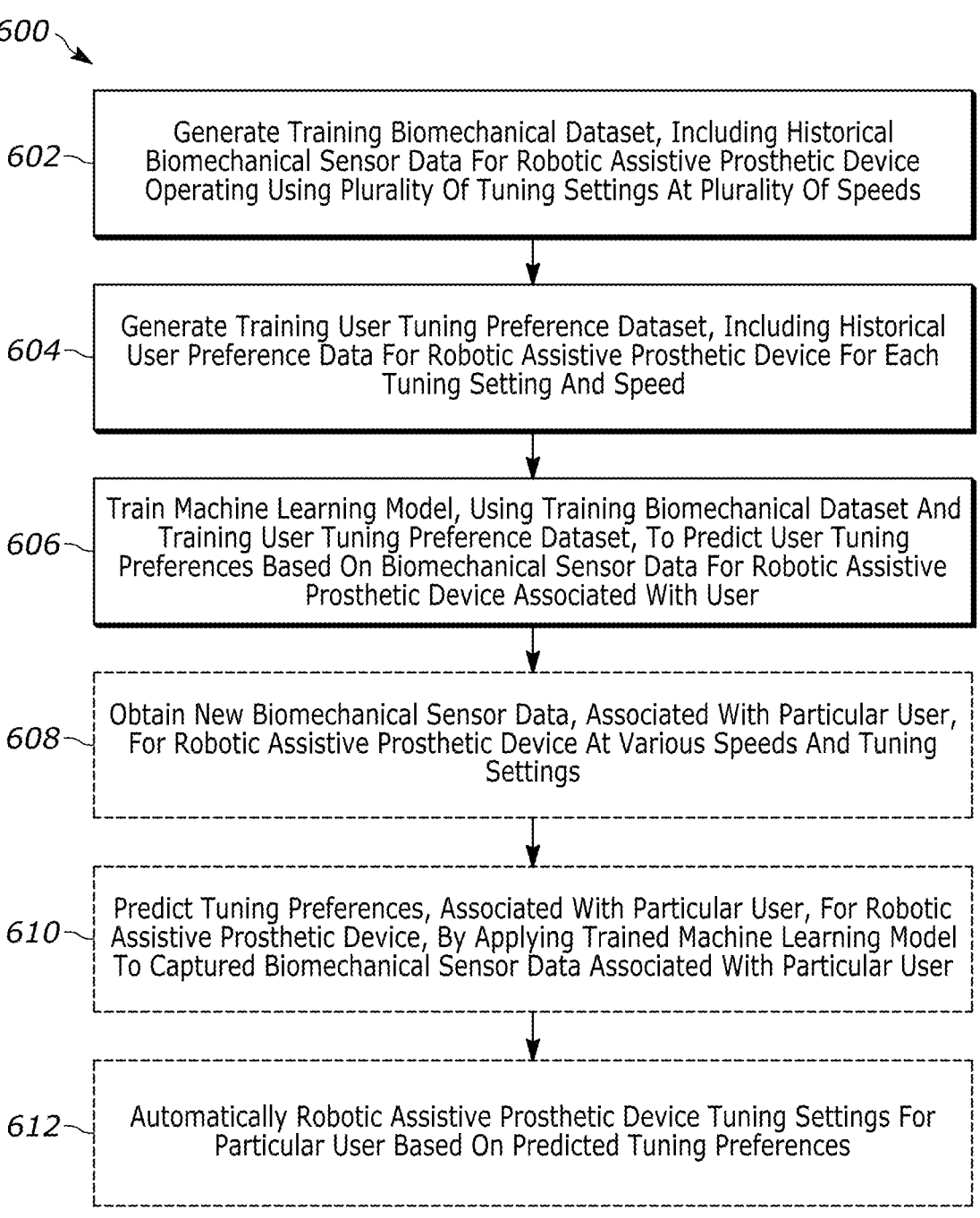

600

602 ~ Generate Training Biomechanical Dataset, Including Historical Biomechanical Sensor Data For Robotic Assistive Prosthetic Device Operating Using Plurality Of Tuning Settings At Plurality Of Speeds 604 ~ Generate Training User Tuning Preference Dataset, Including Historical User Preference Data For Robotic Assistive Prosthetic Device For Each Tuning Setting And Speed 606 ~ Train Machine Learning Model, Using Training Biomechanical Dataset And Training User Tuning Preference Dataset, To Predict User Tuning Preferences Based On Biomechanical Sensor Data For Robotic Assistive Prosthetic Device Associated With User 608 ~ Obtain New Biomechanical Sensor Data, Associated With Particular User, For Robotic Assistive Prosthetic Device At Various Speeds And Tuning Settings 610 ~ Predict Tuning Preferences, Associated With Particular User, For Robotic Assistive Prosthetic Device, By Applying Trained Machine Learning Model To Captured Biomechanical Sensor Data Associated With Particular User 612 ~ Automatically Robotic Assistive Prosthetic Device Tuning Settings For Particular User Based On Predicted Tuning Preferences

FIG. 6

Table I: Biomechanical Signal Subsets.

| Subset | Signals | Body Part | # Of Signals |
|---|---|---|---|
| All | IK | Bilateral Hip, Knee, Ankle | 10 |
| | ID | Bilateral Hip, Knee, Ankle | 10 |
| | GRF/COP | Bilateral | 10 |
| | SK | Bilateral Foot, Shank, Thigh & Pelvis | 63 |
| Total | | | S=93 |
| Affected Side | IK | Affected Hip, Knee, Ankle | 5 |
| | ID | Affected Hip, Knee, Ankle | 5 |
| | GRF/COP | Affected Side | 5 |
| | SK | Affected Foot, Shank, Thigh | 27 |
| Total | | | S=42 |
| Affected Side Foot/Shank | IK | Affected Ankle | 1 |
| | ID | Affected Ankle | 1 |
| | GRF/COP | Affected Side | 5 |
| | SK | Affected Foot, Shank | 18 |
| Total | | | S=25 |

FIG. 7

Table II: Mean Error (% User's Preferred Stiffness)

| Machine Learning Algorithms | All Data | | Affected Side Data | | Affected Side Foot And Shank Data | |
|---|---|---|---|---|---|---|
| | Sub. Dep. | Sub. Ind. | Sub. Dep. | Sub. Ind. | Sub. Dep. | Sub. Ind. |
| KNN | -0.3 ± 12.3 | 2.1 ± 22.0 | -0.5 ± 11.8 | 4.1± 20.5 | 0.1 ± 13.1 | 4.3 ± 20.4 |
| SVR | 0.2 ± 6.9 | 4.5 ± 18.1 | 0.2 ± 7.9 | 12.9± 19.0 | 0.2 ± 8.9 | 13.3 ± 19.7 |
| ANN | 0.3 ± 5.5 | 8.5 ± 16.5 | -0.8 ± 5.6 | 6.5± 16.9 | -0.9 ± 6.0 | -3.8 ± 17.8 |
| CNN | 0.3 ± 6.2 | 8.6 ± 17.1 | -0.4 ± 5.8 | 11.0± 14.6 | 1.2 ± 6.3 | 8.2 ± 14.9 |
| LSTM | -0.1 ± 5.7 | 5.3 ± 17.8 | 0.2 ± 5.2 | 7.1± 16.5 | -0.1 ± 5.7 | 4.1 ± 16.0 |

Table III: Root Mean Square Error (RMSE) (% User's Preferred Stiffness)

| Machine Learning Algorithms | All Data | | Affected Side Data | | Affected Side Foot/Shank Data | |
|---|---|---|---|---|---|---|
| | Sub. Dep. | Sub. Ind. | Sub. Dep. | Sub. Ind. | Sub. Dep. | Sub. Ind. |
| KNN | 12.3 ± 0.2 | 24.5 ± 2.0 | 11.8 ± 0.2 | 24.3± 4.1 | 13.1 ± 0.1 | 24.2 ± 5.7 |
| SVR | 6.9 ± 0.2 | 26.0 ± 12.0 | 7.9 ± 0.5 | 25.5± 10.4 | 8.9 ± 0.4 | 28.1 ± 13.6 |
| ANN | 5.8 ± 0.5 | 20.4 ± 6.7 | 5.7 ± 0.3 | 21.3± 6.7 | 6.1 ± 0.2 | 23.0 ± 9.1 |
| CNN | 6.3 ± 0.2 | 23.3 ± 6.4 | 5.9 ± 0.4 | 19.7± 6.4 | 6.5 ± 0.2 | 21.7 ± 8.6 |
| LSTM | 5.7 ± 0.4 | 22.6 ± 6.3 | 5.2 ± 0.3 | 20.5± 6.4 | 5.7 ± 0.3 | 20.9 ± 4.7 |

FIG. 7 (Continued)

PREDICTING USER PREFERENCE WITH AI TO CONTROL A NEW GENERATION OF WEARABLE ASSISTIVE TECHNOLOGIES

FIELD OF THE DISCLOSURE

The present disclosure generally relates to robotic assistive prostheses and, more particularly, to techniques for using machine learning methods to predict user preferences with respect to robotic assistive prostheses and/or custom tune the robotic assistive prostheses for individual users based on the predicted user preferences.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Emerging variable-stiffness ankle prostheses can modulate their stiffness to meet differing biomechanical demands. To this end, knowledge of the optimal ankle stiffness is required for each user and activity. One approach to is to match the stiffness of prosthesis to the user's preference, but this requires a time consuming tuning process to determine each user's preferences.

SUMMARY

As disclosed herein, user-preferred ankle stiffness is estimated using biomechanical data collected from seven subjects during walking at stiffness settings around their preferred stiffness. Different machine learning algorithms, sensor subsets, and the impact of user-specific training data on estimation accuracy were investigated. A long short term memory (LSTM) algorithm trained on user-specific data from the affected side only was able to predict user preferred ankle stiffness with an root mean square error (RMSE) of 5.2%±0.3%. The prediction error was less than prosthesis users' ability to reliably sense stiffness changes (7.7%), which highlights the significance of the performance of the method provided herein. This disclosure provides the foundation for an automated approach for predicting user-preferred prosthesis mechanics that would ease the burden of tuning these systems in a clinical setting.

In one aspect, a computer-implemented method is provided, comprising: generating, by one or more processors, a training biomechanical dataset, including historical biomechanical sensor data for a plurality of users operating a robotic assistive prosthetic device using a plurality of tuning settings at a plurality of speeds; generating, by the one or more processors, a training user preference dataset including historical user tuning preference data for the plurality of users for each respective tuning setting and speed of the robotic assistive prosthetic device; and training, by the one or more processors, using the training biomechanical dataset and the training user preference dataset, a robotic assistive prosthetic device tuning preference machine learning model to predict user tuning preferences for the robotic assistive prosthetic device based on biomechanical sensor data for the robotic assistive prosthetic device associated with a user.

In some examples, the computer-method further includes obtaining, by the one or more processors, new biomechanical sensor data, associated with a particular user, for the robotic assistive prosthetic device operating using the plurality of tuning settings at the plurality of speeds; and applying, by the one or more processors, the trained robotic assistive prosthetic device tuning preference machine learning model to the new biomechanical sensor data associated with the particular user to predict user tuning preference data for the robotic assistive prosthetic device.

Furthermore, in some examples, the computer-implemented method further includes automatically modifying, by the one or more processors, tuning settings for the robotic assistive prosthetic device based on the predicted user tuning preference data.

Additionally, in some examples, at least a portion of the new biomechanical sensor data and/or the historical biomechanical sensor data is captured by onboard sensors of the robotic assistive prosthetic device.

Moreover, in some examples, the new biomechanical sensor data and/or the historical sensor data each include one or more of: bilateral three degree-of-freedom (3-DOF) hip angle data, sagittal knee angle data, sagittal ankle angle data, bilateral 3-DOF hip moment data, sagittal knee moment data, and sagittal ankle moment data, bilateral 3-DOF ground reaction force, anterior center of pressure (COP) data, posterior COP data, mediolateral COP data, 3-DOF position of pelvis data, 3-DOF position of bilateral foot data, 3-DOF position of shank data, 3-DOF position of thigh data, 3-DOF velocity of pelvis data, 3-DOF velocity of bilateral foot data, 3-DOF velocity of shank data, 3-DOF velocity of thigh data, 3-DOF acceleration of pelvis data, 3-DOF acceleration of bilateral foot data, 3-DOF acceleration of shank data, or 3-DOF acceleration of thigh data.

In some examples, the new biomechanical sensor data and/or the historical sensor data are captured for each stride of the robotic assistive prosthetic device.

In another aspect, a system is provided, comprising: a robotic assistive prosthetic device; one or more processors; and a memory storing non-transitory computer-readable instructions that, when executed by the one or more processors, cause the one or more processors to: generate a training biomechanical dataset, including historical biomechanical sensor data for a plurality of users operating the robotic assistive prosthetic device using a plurality of tuning settings at a plurality of speeds; generate a training user preference dataset including historical user tuning preference data for the plurality of users for each respective tuning setting and speed of the robotic assistive prosthetic device; and train, using the training biomechanical dataset and the training user preference dataset, a robotic assistive prosthetic device tuning preference machine learning model to predict user tuning preferences for the robotic assistive prosthetic device based on biomechanical sensor data for the robotic assistive prosthetic device associated with a user.

In some examples, the computer-readable instructions, when executed by the one or more processors, further cause the one or more processors to: obtain new biomechanical sensor data, associated with a particular user, for the robotic assistive prosthetic device operating using the plurality of tuning settings at the plurality of speeds; and apply the trained robotic assistive prosthetic device tuning preference machine learning model to the new biomechanical sensor data associated with the particular user to predict user tuning preference data for the robotic assistive prosthetic device.

Additionally, in some examples, the computer-readable instructions, when executed by the one or more processors, further cause the one or more processors to automatically modify tuning settings for the robotic assistive prosthetic device based on the predicted user tuning preference data.

Furthermore, in some examples, the robotic assistive prosthetic device includes one or more onboard sensors configured to capture at least a portion of the new biomechanical sensor data and/or the historical biomechanical sensor data.

Moreover, in some examples, the new biomechanical sensor data and/or the historical sensor data each include one or more of: bilateral three degree-of-freedom (3-DOF) hip angle data, sagittal knee angle data, sagittal ankle angle data, bilateral 3-DOF hip moment data, sagittal knee moment data, and sagittal ankle moment data, bilateral 3-DOF ground reaction force, anterior center of pressure (COP) data, posterior COP data, mediolateral COP data, 3-DOF position of pelvis data, 3-DOF position of bilateral foot data, 3-DOF position of shank data, 3-DOF position of thigh data, 3-DOF velocity of pelvis data, 3-DOF velocity of bilateral foot data, 3-DOF velocity of shank data, 3-DOF velocity of thigh data, 3-DOF acceleration of pelvis data, 3-DOF acceleration of bilateral foot data, 3-DOF acceleration of shank data, or 3-DOF acceleration of thigh data.

In some examples, the new biomechanical sensor data and/or the historical sensor data are captured for each stride of the robotic assistive prosthetic device.

In still another aspect, a non-transitory computer-readable medium is provided, storing instructions that, when executed by one or more processors, cause the one or more processors to: generate a training biomechanical dataset, including historical biomechanical sensor data for a plurality of users operating a robotic assistive prosthetic device using a plurality of tuning settings at a plurality of speeds; generate a training user preference dataset including historical user tuning preference data for the plurality of users for each respective tuning setting and speed of the robotic assistive prosthetic device; and train, using the training biomechanical dataset and the training user preference dataset, a robotic assistive prosthetic device tuning preference machine learning model to predict user tuning preferences for the robotic assistive prosthetic device based on biomechanical sensor data for the robotic assistive prosthetic device associated with a user.

In some examples, the instructions, when executed by the one or more processors, further cause the one or more processors to: obtain new biomechanical sensor data, associated with a particular user, for the robotic assistive prosthetic device operating using the plurality of tuning settings at the plurality of speeds; and apply the trained robotic assistive prosthetic device tuning preference machine learning model to the new biomechanical sensor data associated with the particular user to predict user tuning preference data for the robotic assistive prosthetic device.

Additionally, in some examples, the instructions, when executed by the one or more processors, further cause the one or more processors to automatically modify tuning settings for the robotic assistive prosthetic device based on the predicted user tuning preference data.

Furthermore, in some examples, at least a portion of the new biomechanical sensor data and/or the historical biomechanical sensor data is captured by onboard sensors of the robotic assistive prosthetic device.

Moreover, in some examples, the new biomechanical sensor data and/or the historical sensor data each include one or more of: bilateral three degree-of-freedom (3-DOF) hip angle data, sagittal knee angle data, sagittal ankle angle data, bilateral 3-DOF hip moment data, sagittal knee moment data, and sagittal ankle moment data, bilateral 3-DOF ground reaction force, anterior center of pressure (COP) data, posterior COP data, mediolateral COP data, 3-DOF position of pelvis data, 3-DOF position of bilateral foot data, 3-DOF position of shank data, 3-DOF position of thigh data, 3-DOF velocity of pelvis data, 3-DOF velocity of bilateral foot data, 3-DOF velocity of shank data, 3-DOF velocity of thigh data, 3-DOF acceleration of pelvis data, 3-DOF acceleration of bilateral foot data, 3-DOF acceleration of shank data, or 3-DOF acceleration of thigh data.

In some examples, the new biomechanical sensor data and/or the historical sensor data are captured for each stride of the robotic assistive prosthetic device.

BRIEF DESCRIPTION OF THE DRAWINGS

FIG. 6 illustrates a flow diagram of an example method for using machine learning methods to predict user preferences with respect to robotic assistive prostheses and/or custom tune the robotic assistive prostheses for individual users based on the predicted user preferences, in accordance with some embodiments.

FIG. 7 illustrates Table I, Table II, and Table III. Table I illustrates three signal subsets: All Data, Affected Side Data, and Affected Side Foot/Shank Data. Each signal subset includes signals from inverse kinematics (IK), inverse dynamics (ID), ground reaction forces (GRF), center of pressure (COP), and segment kinematics (SK). S denotes the total number of signals in each signal subset.

Figure 1B:
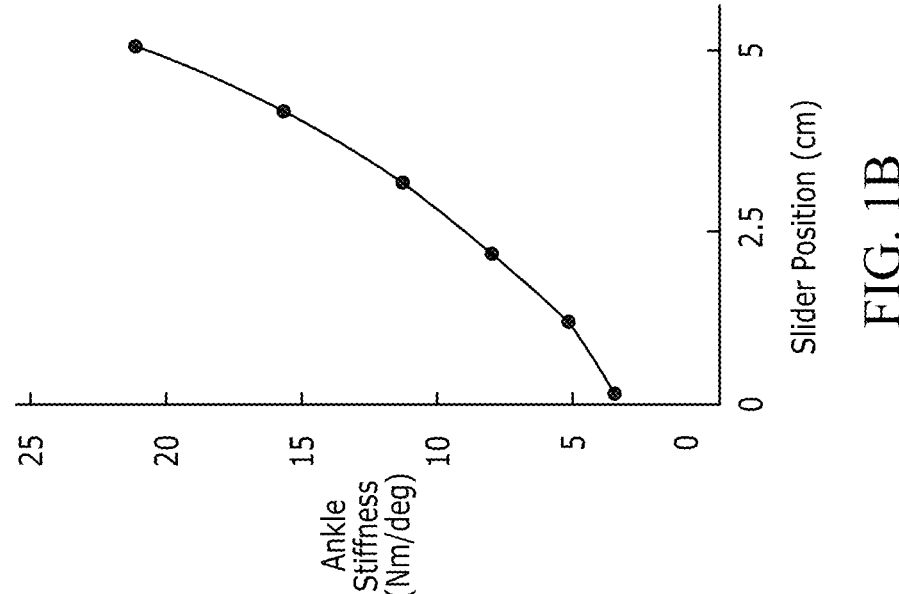
FIG. 1B illustrates a range of available dorsiflexion stiffness values possible by adjusting the sliding support of the VSPA Foot shown at FIG. 1A.

Table II illustrates the mean and standard deviation (mean±SD) of the error as calculated across all data points from 7 folds of the cross validation. Results are shown for the five machine learning algorithms: K-Nearest Neighbor (KNN), Support Vector Regression (SVR), Artificial Neural Network (ANN), Convolutional Neural Network (CNN), and Long Short Term Memory Network (LSTM). Each algorithm was evaluated using three signal subsets: All Data, Affected Side Data, and Affected Side Foot/Shank Data, and two data splitting methods: Subject Dependent (Sub. Dep.) and Subject Independent (Sub. Ind.).

Table III illustrates the mean and standard deviation (mean±SD) of the root mean square error (RMSE) as calculated across 7 folds of the cross validation. Results are shown for the five machine learning algorithms: K-Nearest Neighbor (KNN), Support Vector Regression (SVR), Artificial Neural Network (ANN), Convolutional Neural Network (CNN), and Long Short Term Memory Network (LSTM). Each algorithm was evaluated using three signal subsets: All Data, Affected Side Data, and Affected Side Foot/Shank Data (see Table I), and two data splitting methods: Subject Dependent (Sub. Dep.) and Subject Independent (Sub. Ind.). A Bold number represent the best performing (lowest RMSE) ML algorithms across all signal subsets and data splitting methods.

DETAILED DESCRIPTION

Overview

Robotic assistive technologies—such as exoskeletons and robotic prostheses—hold the potential to transform the mobility of people with disabilities. These technologies provide mechanical assistance to their wearer that is able to help offset the biomechanical deficits associated with neuromotor pathologies (e.g. limb loss). For example, when using conventional, passive ankle-foot prostheses, people with below-knee amputations walk slower, are less stable, and fatigue more quickly. Over the past decades, researchers have developed advanced prostheses that seek to address these deficits. Recently developed powered prostheses can have challenges with cost, size, weight, and robustness. Consequently, many researchers have pursued a different approach—termed quasi-passive prostheses—that use a small motor and battery to adjust the system's mechanical properties without enabling net-positive mechanical work. These systems are often smaller, lighter, and lower cost when compared to fully powered versions. Thus, quasi-passive prostheses attempt to strike a balance between the function provided by more sophistical mechanisms and the challenges associated with the increased mass and complexity.

A promising and emerging type of quasi-passive prostheses can continuously vary their stiffness from step to step. Different tasks, such as walking or stair ascent, have different kinetic and kinematic demands that cannot be achieved with conventional prostheses. Variable-stiffness prostheses are able to more closely match the demands of different activities while being able to store and return energy to the wearer. Recent approaches to develop variable-stiffness prostheses have focused on the implementation of variable-length leaf springs and shear thickening fluids. These systems often have a single variable (e.g. the length of the internal leaf spring) that must be properly "tuned" or adjusted to match the desired kinetic and kinematic patterns.

An open and important research question pertains to how to effectively set the optimal prosthesis stiffness across users and activities. Researchers have proposed to tune the mechanics of assistive technologies to meet specific physiological or biomechanical objectives. A common physiological objective is to reduce the metabolic rate of the wearer. This approach is often combined with an automatic tuning process, a strategy known as "human-in-the-loop"

optimization. However, in actuality, prosthesis users likely have shifting objectives depending on the activity or task of the user. These objectives may be influenced by quantitative and qualitative factors (e.g. stability, comfort, etc.), which can be difficult or impossible to measure. Instead, leverage user preference may be leveraged as a holistic objective that is able to capture the quantitative and qualitative attributes of user experience. That is, by including the user's perception of their experience—their preferences—the user may be used as both the sensor and optimizer to determine the stiffness that maximizes their experience.

Researchers have begun to investigate the role of user preference in the control of assistive technologies. For instance, there exists an online tuning process to optimize user preference based on Bayesian methods. Their approach used forced choice experiments with co-active feedback to tune the step trajectory parameters of a lower-limb exoskeleton. Some groups have used a self-tuning process to identify user preference, wherein instead of using a forced choice method, users adjust the control parameters to obtain their preferred setting. As provide herein, the stiffness preferences of both people with amputations and the clinicians that prescribe prostheses have been quantified. Generally speaking, prosthesis users have diverse yet consistent preferences. In addition, as provided herein, the preferred stiffness of prosthesis users generally maximized their kinematic symmetry at the ankle joint. However, identifying user preference typically involves a self-tuning experimental session that can require specialized engineers to assist, in addition to a lengthy tuning session. In addition, manual preference-based tuning will not likely scale to strategies with a greater number of parameters that must be tuned. Finally, obtaining user preferences for each activity may be infeasible for translation.

To reduce the experimental demands of determining user preference, the present disclosure provides methods in which user preferences may be predicted rather than being obtained experimentally. The overarching hypothesis is that there are consistent features that underlie user preference, which can be used to develop a machine learning model able to predict user preferences from biomechanical data. The hypothesis is supported by common biomechanical trends that emerge across users when walking on a prosthesis with their preferred ankle stiffness. As provided herein, 1) the predictions of user preferred prosthesis ankle stiffness were implemented and compared using two classical machine learning (ML) approaches and three deep learning (DL) approaches, 2) the effects of including subject specific data on the predictions of user's preferred prosthesis ankle stiffness were analyzed and compared, and 3) three groups of biomechanical signals were analyzed and compared to understand the effect of data amount and type on estimation accuracy. The models were trained on a dataset of seven subjects who walked on the variable stiffness ankle prosthesis at stiffness settings around their preferred stiffness. As provided herein, biomechanical data can be used with deep learning models to accurately predict user preferences, but some subject-specific data is likely needed. The present disclosure introduces a new method to identify user's preferred prosthesis stiffness and to develop a preference-based tuning approach that is feasible and convenient to incorporate in a clinical setting.

Methodology

Variable Stiffness Prosthetic Ankle (VSPA) Foot

Figure 1A:
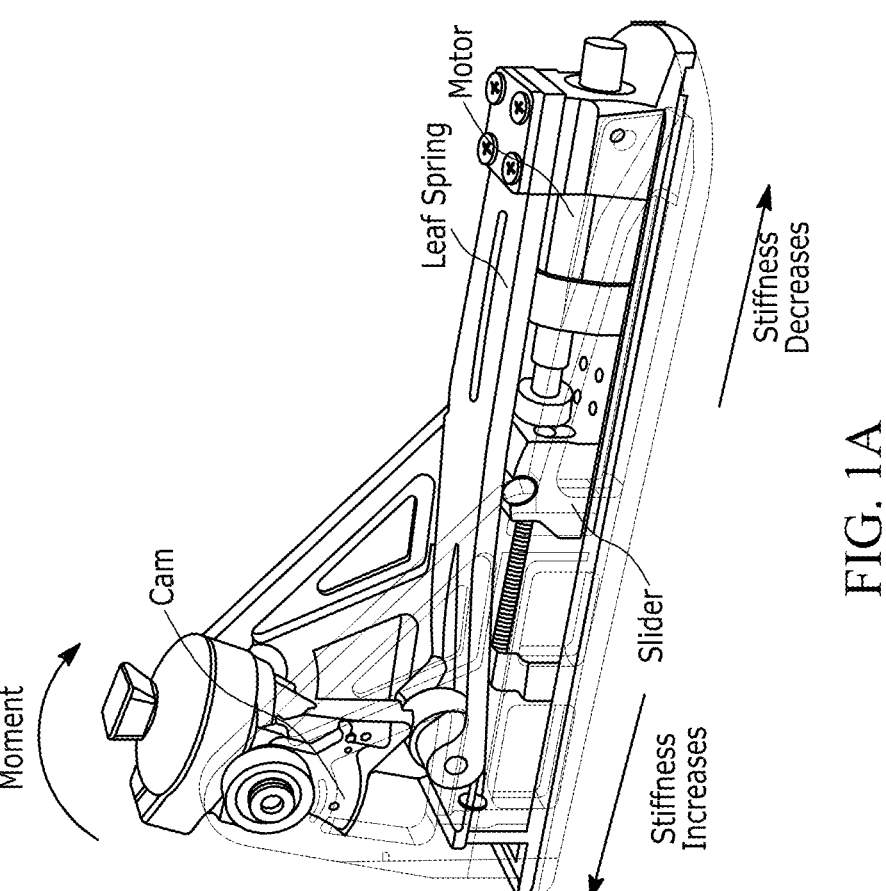
FIG. 1A illustrates a schematic of an example Variable Stiffness Prosthetic Ankle (VSPA) Foot, shown with relevant components highlighted.

The VSPA Foot is a quasi-passive ankle-foot prosthesis that is able to change the stiffness of its ankle joint from step to step. The mechanism uses a variable length leaf spring coupled to a cam-based transmission, as shown at FIG. 1A. The stiffness is adjusted using a small motor that re-positions the support condition of the leaf spring, effectively changing its length. The stiffness can be adjusted during the swing phase of gait, when the ankle is not loaded. The mass of the prototype is approximately 1900 g, and it is able to vary stiffness by nearly an order of magnitude. The mechanism is mechanically passive, but uses a small battery to power the electric motor and embedded system.

Experimental Data Collection

The dataset used in this study provided herein was collected from seven individuals with unilateral transtibial amputation walking with the VSPA Foot. The experimental protocol was divided into two parts: 1) preferred ankle stiffness identification, and 2) lower extremity biomechanical data collection. During the preferred ankle stiffness identification procedure, participants donned the VSPA Foot as they walked on the treadmill. They were taught to use a mechanical dial to personally customize the stiffness of the VSPA Foot to identify their preferred stiffness. Within a single preference-identification trial, participants were encouraged to explore the full range of stiffness values from "uncomfortably stiff" to "uncomfortably soft" before determining the stiffness they preferred. Participants performed three preference-identification trials at each of three treadmill speeds, for a total of nine preference-identification trials per subject. For a given treadmill speed, the participant's preferred stiffness was calculated as the average preferred stiffness across the three trials. After the preferred ankle stiffness identification procedure, the lower extremity biomechanical data collection was conducted. Participants walked on the treadmill with the VSPA Foot stiffness set to five different values (70%, 85%, 100%, 115%, 130% of their preferred stiffness) at each of three treadmill speeds. For each treadmill speed, all five stiffness values were tested in a single, consecutive block, with participants continuously walking for 3-4 minutes with a particular stiffness value. While subjects walked on the treadmill, lower-limb biomechanical data were collected using optical motion capture (Vicon Motion Systems Ltd, Oxford, UK). Ground reaction force data were collected using the force plates embedded in the instrumented treadmill (Bertec, Columbus, Ohio). During the data collection, approved consent was obtained from all subjects prior to the study with approval from the University of Michigan Medical School Institutional Review Board.

Dataset

All biomechanical data were post-processed using OpenSim (Stanford University, Palo Alto, Calif.). In total, the dataset comprised 93 biomechanical signals. These signals fell into four categories: inverse kinematics (IK), inverse dynamics (ID), ground reaction forces/center of pressure (GRF/COP), and segment kinematics (SK). The inverse kinematics signals (10 signals) were bilateral 3-DOF hip angle, sagittal knee angle, and sagittal ankle angle. The inverse dynamics signals (10 signals) were bilateral 3-DOF hip moment, sagittal knee moment, and sagittal ankle moment. The ground reaction force signals (10 signals) were bilateral 3-DOF ground reaction force (GRF), and anterior/posterior and mediolateral center of pressure (COP). The segment kinematics signals (63 signals) were 3-DOF position, 3-DOF velocity, and 3-DOF acceleration of the pelvis and bilateral foot, shank, and thigh body segments.

The data was segmented into strides, defined from left heel contact to subsequent left heel contact; one stride contained data from all the signals, each interpolated from 0 to 100% gait cycle (101 data points). Pooled across all subjects and speeds, the final dataset comprises 12080 strides (i.e samples). Each subject had different number of strides taken throughout the experiment, with an average of 1725±306 strides.

To evaluate how training with different biomechanical signals affects prediction performance, the signals were divided into three subsets (Table I, as shown in FIG. 7). The three signal subsets were: 1) All Data, which included all collected signals (93 signals), 2) Affected Side Data, which only included the signals from the user's affected (i.e., prosthetic) side, excluding the pelvis (42 signals), and 3) Affected Side Foot/Shank Data, which only included the signals from the user's affected side foot and shank (25 signals).

Data Preparation

Data Preprocessing

The data was preprocessed to mitigate the effects of noise and irregularities in the dataset and to improve the training efficiency and predictive performance of the algorithms. Two data preprocessing steps were performed: a) Min-Max Normalization and b) Feature Extraction.

Min-Max Normalization

For both classical machine learning (ML) and deep learning (DL) algorithms, Min-Max Normalization was performed to scale the different biomechanical signals in the dataset: $X'=(X-X_{min})/(X_{max}-X_{min})$. For each stride of the biomechanical signals, each data point (X) was normalized with respect to the minimum ($X_{min}$) and maximum ($X_{max}$) observed values to generate the scaled data point (X').

Feature Extraction

For the classical ML models only, feature extraction was performed to remove noise and reduce the model training time. For all biomechanical signals, six features were extracted from each stride: mean, standard deviation, maximum value, minimum value, first value and last value.

Data Splitting

For both classical ML and DL algorithms, the dataset was divided into training, validation, and testing sets in two ways a) Subject Independent and b) Subject Dependent.

Subject Independent

In the Subject Independent case, the machine learning models had no information about the test subject during the training process. In this case, a leave-one-subject-out cross validation was utilized. The training and validation sets included data from six subjects. Approximately 76% of all strides were included in the training set, while 10% were withheld as a validation set. The seventh subject's data were used as the testing set (approximately 14% of all strides). This process was repeated seven times, until all subjects had been left out.

Subject Dependent

In the Subject Dependent case, the machine learning models had some information about all the subjects during the training process. In this case, a 7-fold cross validation was performed. For each fold, the dataset was split into training (76% of all strides), validation (10%) and testing (14%) sets. These percentages were chosen to mirror the distribution of data in the Subject Independent case.

Machine Learning Algorithms

Two classical machine learning (ML) and three deep learning (DL) algorithms were implemented to predict a participant's preferred prosthetic ankle stiffness from biomechanical signals. For all algorithms, the validation set was used to tune the hyperparameters of each model prior to training. A grid search for the hyperparameter tuning was performed, with the objective function of minimizing the root mean square error (RMSE) between the predicted preferred VSPA Foot stiffness and the ground truth preferred VSPA Foot stiffness. For hyperparameter tuning, the entire dataset (All Data) and the Subject Dependent data splitting method were used.

Classical Machine Learning Algorithms

Two classical ML algorithms were implemented using Python's scikit-learn package: a) K-Nearest Neighbor (KNN) and b) Support Vector Regression (SVR). For the classical ML algorithms, the training data were the six features extracted from each stride of the training set. The training data for the classical ML algorithms had dimensions of N× (S.6), where N is the total number of strides in the training set, and S is the number of signals in the biomechanical signal subset (see Table I, as shown in FIG. 7). The training labels (dimension: N×1) were the corresponding ground truth VSPA Foot stiffness, expressed as a percentage of the user's preferred stiffness (i.e. 70%, 85%, 100%, 115%, 130%). To test the classical ML algorithms, each stride of the testing set (dimension: 1×(S.6)) was used as an input to the trained model to predict the corresponding VSPA foot stiffness for that stride. This testing method was selected to evaluate each model's performance when using the minimum amount of data collected from one individual (i.e., one stride).

K-Nearest Neighbor

The KNN algorithm makes predictions based on the similarity of the features in the dataset. The KNN algorithm stores the training data, and the prediction is made based on the weighted average of the distance function for the K nearest points. The Euclidean distance function and a neighbors value of K=5 were selected.

Support Vector Regression

The SVR algorithm makes predictions by first mapping the training dataset to a higher dimension based on the kernel, and then finding a hyperplane with optimal margins in the higher dimension. A third degree polynomial kernel was selected, the regularization parameter was $10^3$, the error sensitivity parameter (f) was 0.1, and the spread of the kernel ($\gamma$) was defined as 1/(number of features×training data variance).

Deep Learning Algorithms

Three DL models were implemented: a) Artificial Neural Network (ANN), b) Convolutional Neural Network (CNN), and c) Long Short Term Memory (LSTM) Network. The mean squared error loss function and a stochastic gradient-based optimizer, ADAM, were used to train the DL models. L1 and L2 regularization were added in addition to the loss function to improve the generalizability of the networks. All calculations were performed using TensorFlow and Keras packages.

For the DL algorithms, the training data were the time-series data (101 data points) of each stride of the training set. For the ANN and LSTM algorithms, the training data had dimensions of N× (S.101), where N is the total number of strides in the training set, and S is the number of signals in the biomechanical signal subset (see Table I, as shown in FIG. 7). For the CNN algorithm, the training data was transformed to be 3-dimensional, with dimensions of N×101×S. The training labels (dimension: N×1) were the corresponding ground truth VSPA Foot stiffness, expressed as a percentage of the user's preferred stiffness (i.e. 70%, 85%, 100%, 115%, 130%). To test the DL algorithms, each stride of the testing set was used as an input to the trained model to predict the corresponding VSPA foot stiffness for that stride. For the ANN and LSTM algorithms, the test data had dimensions of 1×(S.101); for the CNN algorithm, the test data had dimensions of 1×101×S.

Artificial Neural Network

Figure 2:
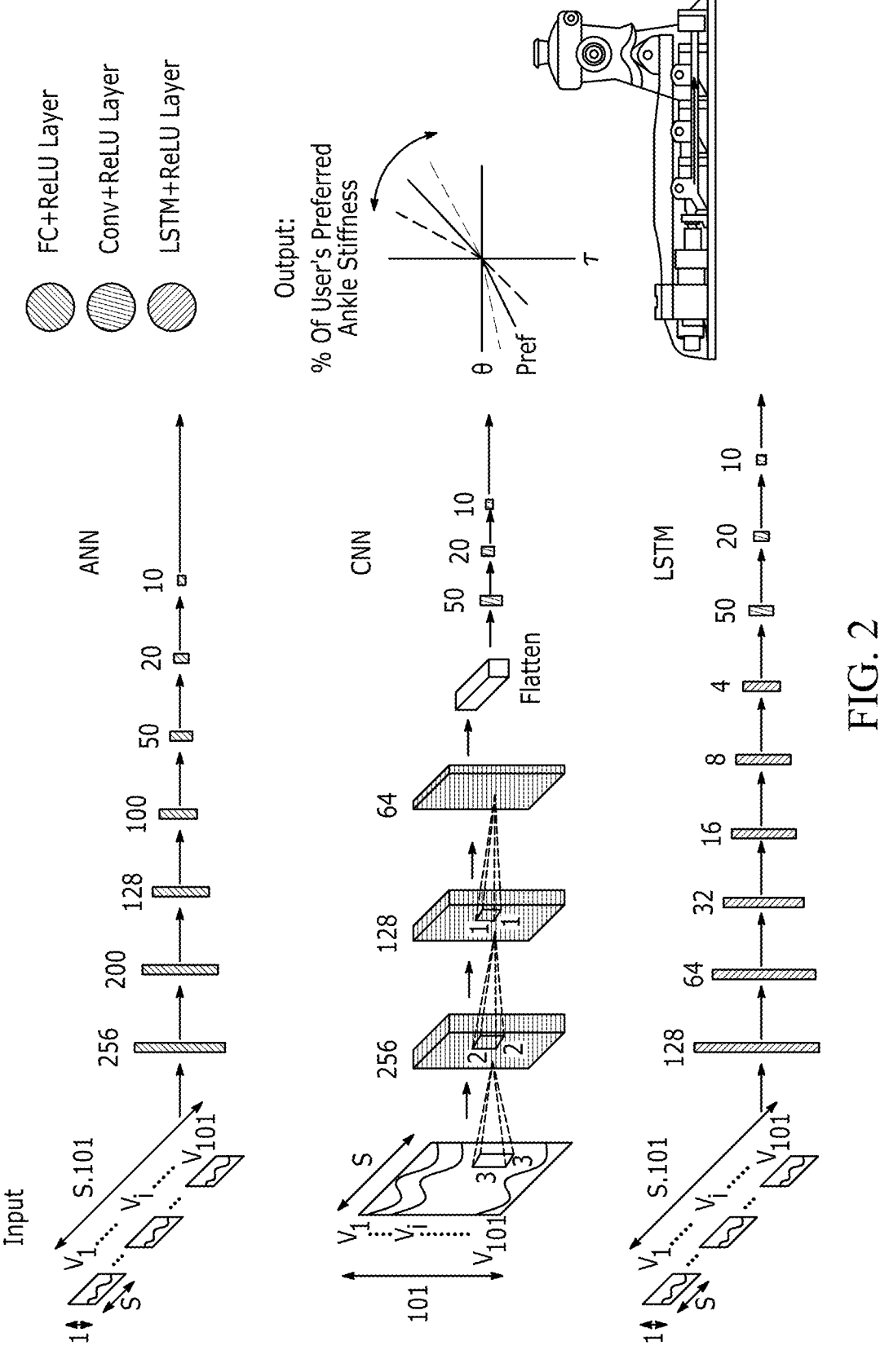
FIG. 2 illustrates a depiction of testing three deep learning algorithms. The input sample is one stride (i.e. gait cycle) of data, which includes the S biomechanical signals of the signal subset (see Table I, as shown in FIG. 7, for the value of S for each signal subset). For the artificial neural network (ANN) and long short term memory (LSTM) algorithms, the input sample size is $1\times(S. 101)$. For the convolutional neural network (CNN) algorithm, the input data is reshaped to the size $101\times S$. The output for all three networks is the VSPA Foot stiffness, expressed as a percentage of the user's preferred ankle stiffness. Vi (dimensions: $1\times S$) is a vector that contains the ith ($1<i<101$) measurement of the gait cycle, concatenated for the S biomechanical signals.

The ANN architecture comprised 7 fully-connected dense layers with 256, 200, 128, 100, 50, 20, and 10 units, as shown at FIG. 2. Rectified Linear Units (ReLU) were used as the activation function to account for nonlinearity. A batch size of 128 was selected and 300 epochs were used. The learning rate was $10^{-3}$, the decay rate was $10^{-5}$, 300 epochs, the L1 regularization parameter was $10^{-4}$, and the L2 regularization parameter was $10^{-2}$.

Convolutional Neural Network

The CNN models consisted of convolutional layers followed by fully connected layers. The CNN architecture had 256, 128, and 64 filters, with kernel sizes of 3×3, 2×2 and 1×1, respectively, with stride of 1, as shown at FIG. 2. ReLU were used as activation functions. A batch size of 128 was selected and 100 epochs were used. The learning rate was 10–3, the decay rate was 10–5, the L1 regularization parameter was 10–4, and the L2 regularization parameter was 10–3.

Long Short Term Memory Network

The LSTM network was implemented to account for the time-dependency of the biomechanical input signals. The LSTM architecture comprised 6 LSTM layers with 128, 64, 32, 16, 8, and 4 units, followed by 3 fully connected layers, as shown at FIG. 2. ReLU were used as activation functions. A batch size of 128 was selected and 400 epochs were used. The learning rate was 10–4, the decay rate was 10–5, the L1 regularization parameter was 10–4, and the L2 regularization parameter was 10–2.

Data Analysis and Statistics

Five machine learning algorithms (KNN, SVR, ANN, CNN, LSTM), three subsets of biomechanical signals (All Data, Affected Side Data, Affected Side Foot/Shank Data) and two training methods (Subject Dependent, Subject Independent) were evaluated—in total 30 different models were evaluated. The performance of all models was evaluated by calculating two types of error: 1) the mean and standard deviation of error, and 2) the root mean square error (RMSE).

The error was the difference between the predicted VSPA Foot stiffness and the ground truth VSPA Foot stiffness. The mean and standard deviation of error were computed across all predicted data points for all folds of the cross validation. The mean and standard deviation of the error were used to examine the distribution of the model errors.

The RMSE was calculated for each of the 7 folds of the cross validation, and the mean and standard deviation of RMSE were computed across folds. RMSE was calculated to evaluate the magnitude of the error; a lower RMSE indicates better prediction. Using the mean RMSE values from each of the 30 models, a three-way ANOVA was performed; the outcome was RMSE, and the fixed factors were machine learning algorithm, biomechanical signal subset, and training method (i.e., Subject Dependent or Subject Independent). The main effects of the ANOVA were evaluated at a significance value of $\alpha$=0.05.

Results

Figure 3A:
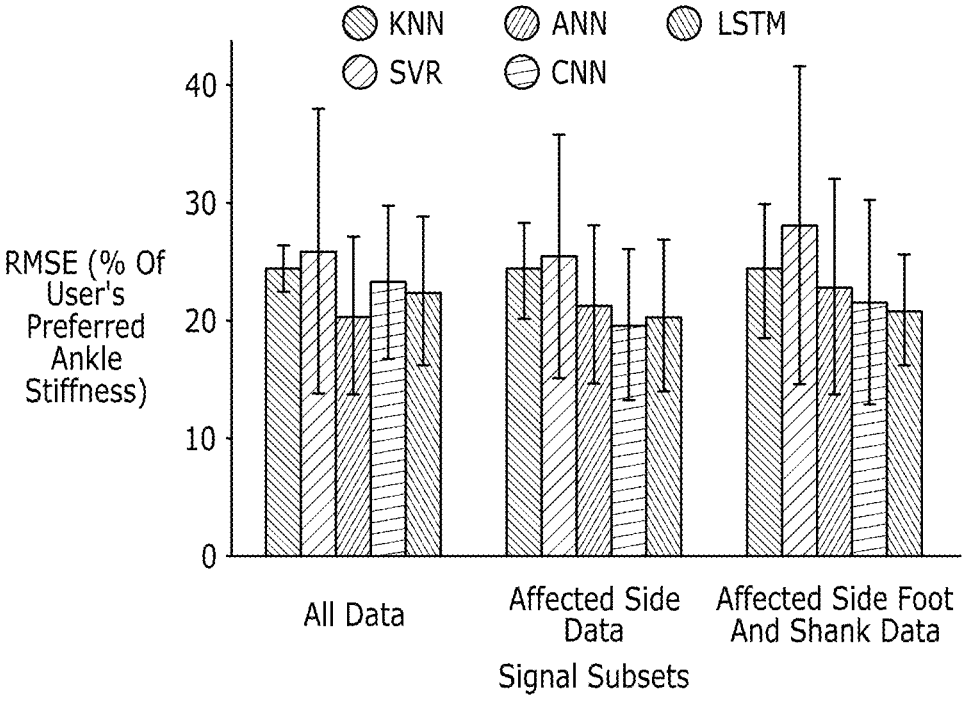
FIGS. 3A and 3B illustrate model performance for Subject Independent and Subject Dependent training methods, respectively. Red bars denote the mean root mean square error (RMSE) and black error bars denote the standard deviation of RMSE, calculated across seven folds of the cross validation. Results are shown for all five machine learning algorithms and three biomechanical signal subsets.
Figure 3B:
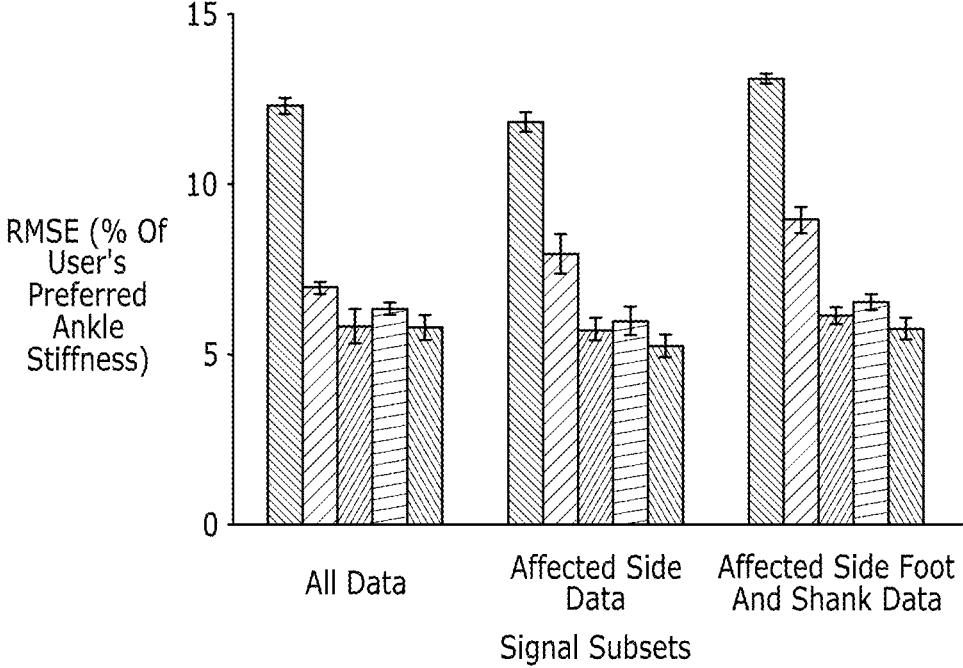

All data are represented as a percentage error from the user's preferred prosthetic ankle stiffness. The mean and standard deviation of error for all 30 models is presented in Table II (as shown in FIG. 7); the mean and standard deviation of RMSE is presented in Table III (as shown in FIG. 7) and FIG. 3.

There was a significant effect of training method on RMSE (ANOVA, p<0.0001). Including subject-specific data in the training process (i.e., the Subject Dependent case) resulted in 67% lower RMSE. Pooled across all machine learning algorithms and signal subsets, the RMSE for Subject Dependent training was 7.6%±2.6%, and for Subject Independent training was 23.1%±2.3% (mean±SD).

There was a significant effect of machine learning algorithm on RMSE (ANOVA, p<0.0001). The three deep learning models (ANN, CNN, LSTM) performed better (i.e., had lower RMSE) than the two classical machine learning models (KNN, SVR). Pooled across training methods and signal subsets, LSTM had the lowest RMSE of 13.4%±7.9%; KNN had the highest RMSE of 18.3%±6.0% (mean±SD).

No significant effect of signal subset was detected on RMSE (ANOVA, p=0.35). Pooled across training methods and machine learning algorithms, the RMSE was 15.4%±8.3% for All Data, 14.8%±7.8% for Affected Side Data, and 15.8%±8.2% for Affected Side Foot/Shank Data (mean±SD).

For the Subject Dependent case (i.e. subject-specific data included in the training set), the LSTM network trained with Affected Side Data had the lowest RMSE of 5.2%±0.3% (mean±SD). For the Subject Independent case, the CNN trained with Affected Side Data had the lowest RMSE of 19.7%±6.4% (mean±SD).

Discussion

This disclosure provides a machine learning (ML) based approach for predicting the user's preferred prosthetic ankle stiffness. To this end, five different ML architectures that estimate the user's preferred stiffness settings from lower extremity biomechanical data were implemented and compared. The effects of subject-specific data and biomechanical signal subsets used when training and estimating the user's preferred prosthesis stiffness were studied. As provided herein, this is a first step toward reducing the time-consuming experimental tuning process needed to identify user preferences.

Effect of Training with Subject-Specific Data

The inclusion of subject-specific training data significantly improved the algorithms' ability to estimate user preferred ankle stiffness. Some biomechanical features (e.g. kinematic symmetry) have recently been shown to be consistent across users when walking at their preferred prosthetic ankle stiffness. However, despite these consistencies, the mean RMS error across all ML models trained on all three biomechanical signal subsets decreased from 23.1% to 7.6% when subject specific data were included. Using these distributions, the best performing ML model (LSTM) would predict a stiffness that would fall within 7.7% of the user's preferred stiffness with a likelihood of 41.5% without subject-specific data, and 99.9% when subject-specific data are included in the training set. This likelihood describes the probability that the LSTM-based approach would predict a stiffness that is imperceptibly close to their preference; it has previously been shown that prosthesis users are unable to reliably sense stiffness changes less than 7.7% (i.e. JND=7.7%). Consequently, a clinical viable solution would require some level of data from the current user's biomechanics to accurately estimate user preferred stiffness within an imperceptible range.

Effect of Machine Learning Algorithms

The three deep learning (DL) models (ANN, CNN, LSTM) performed better than the two classical ML (KNN, SVR) models for all subjects and sensor subsets (biomechanical signal groupings). This may indicate that the DL models are able to extract meaningful features from users' biomechanics that facilitate the estimation of user's preferred ankle stiffness. In addition, the features used with the classical ML methods were selected based on previous work. The hand-crafted features included each stride mean, standard deviation, maximum value, minimum value, first value and last value for all biomechanical signals, which have shown promising results in activity recognition and prosthesis control. However, these features may not be optimal and could be the focus of future investigations.

Effect of Signal Subset Used in Training the ML Algorithms

The amount and location of biomechanical data included did not improve estimation accuracy when predicting user preferred ankle stiffness. This is especially interesting because the amount of biomechanical data varied greatly between conditions. For example, when all data were included, there were 93 time-series signals compared to 25 signals when only data from the affected foot and shank were included. Thus, most of the biomechanical information required to estimate user-preferred prosthesis stiffness are included in the sensors local to the prosthesis. The relative insensitivity of the estimation error to the amount of data included is helpful for potential clinical applications. It is more convenient to obtain data from sensors within the prosthesis, which do not have the challenges associated with implementing sensors on other aspects of the body (e.g. discomfort, obtrusiveness, communication etc.).

Significance to Control of Wearable Robots

Leveraging user preference is a promising approach for the design and tuning of wearable robotic systems; however, the time required to obtain data on user preference can be limiting. Thus, as provided herein, user preferred ankle stiffness was estimated from biomechanical data. The results demonstrate that prediction of user preferred stiffness is possible using biomechanical data, but the approach likely needs to include some user-specific biomechanical data for training. One potential solution could be to acquire training data for a smaller subset of activities, which can be used to predict the preferences and biomechanical trends of other activities. This approach could provide both the benefits of reduced experimental duration while enabling user preference as a method to adjust the stiffness (or other factors) of novel prostheses. In addition, the study provided herein showed little drop in performance as the dataset was expanded to include biomechanical information about other joints or legs. This is encouraging because it indicates that sensor data beyond what can be collected on the prosthesis may not be required for accurate prediction of a user's preferred stiffness. Thus, while user-specific data is likely needed, accurate estimation of user preferred stiffness is likely possible using only data included from the onboard sensors.

Example System

Figure 4:
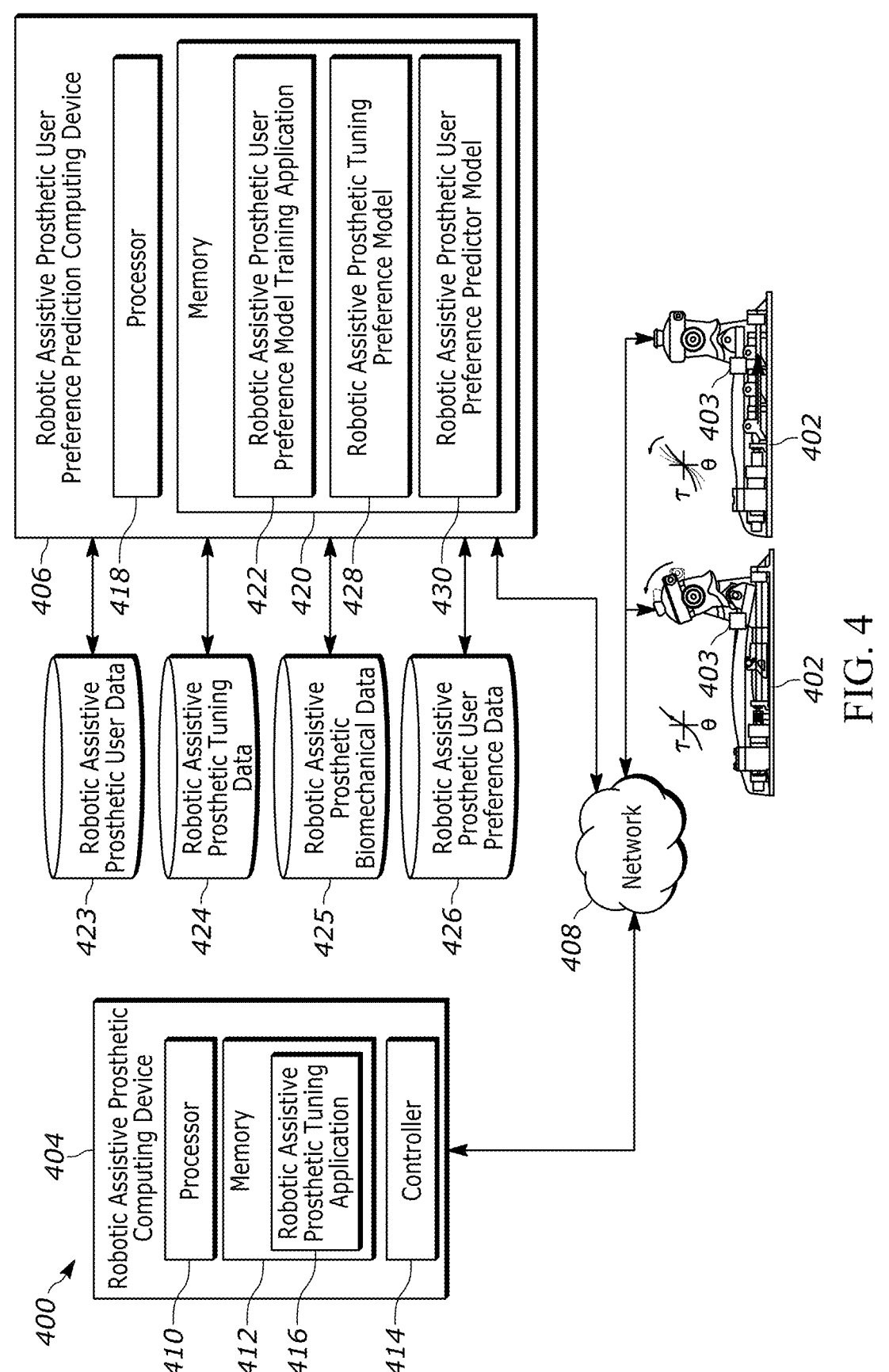
FIG. 4 illustrates a block diagram of an example system for using machine learning methods to predict user preferences with respect to robotic assistive prostheses and/or custom tune the robotic assistive prostheses for individual users based on the predicted user preferences, in accordance with some embodiments.

FIG. 4 illustrates a block diagram of an example system 400 for using machine learning methods to predict user preferences with respect to robotic assistive prostheses and custom tune the robotic assistive prostheses for individual users based on the predicted user preferences, in accordance with some embodiments. The high-level architecture illustrated in FIG. 4 may include both hardware and software applications, as well as various data communications channels for communicating data between the various hardware and software components, as is described below.

The system 400 may include a robotic assistive prosthetic device 402, which may include one or more onboard sensors 403, a robotic assistive prosthetic computing device 404 (which may be onboard the robotic assistive prosthetic device 402 or may be separate from the robotic assistive prosthetic device 402, in various embodiments), a robotic assistive prosthetic user preference prediction computing device 406, as well as one or more other computing devices in some examples. The robotic assistive prosthetic device 402, and the computing devices 404 and 406, may communicate with one another via a network 408, which may be a wired or wireless network, or via various short-range signals, such as Bluetooth®. While the computing devices 404 and 406 are described below as having separate functionality, in some examples, the computing device 404 may perform any of the functions described as being performed by the computing device 406, and vice versa. Moreover, in some examples, there may be a single computing device that performs all functionality described as being performed by the computing devices 404 and 406, or additional/alternative computing devices (not shown) may perform the functionality described as being performed by the computing devices 404 and/or 406.

The robotic assistive prosthetic device 402 may be, for instance, a VSPA Foot device as discussed above. Generally speaking, the robotic assistive prosthetic device 402 may be a prosthetic device operated by a user, e.g., to assist in walking, running, or other movement, and may be configured with one or more tunable settings, such as an ankle stiffness setting, which may be modified for various individual users.

In some examples, the robotic assistive prosthetic device 402 may include one or more onboard sensors 403 configured to capture biomechanical data associated with a user's use of the robotic assistive prosthetic device 402, including, e.g., stride by stride data including bilateral three degree-of-freedom (3-DOF) hip angle data, sagittal knee angle data, sagittal ankle angle data, bilateral 3-DOF hip moment data, sagittal knee moment data, and sagittal ankle moment data, bilateral 3-DOF ground reaction force, anterior center of pressure (COP) data, posterior COP data, mediolateral COP data, 3-DOF position of pelvis data, 3-DOF position of bilateral foot data, 3-DOF position of shank data, 3-DOF position of thigh data, 3-DOF velocity of pelvis data, 3-DOF velocity of bilateral foot data, 3-DOF velocity of shank data, 3-DOF velocity of thigh data, 3-DOF acceleration of pelvis data, 3-DOF acceleration of bilateral foot data, 3-DOF acceleration of shank data, or 3-DOF acceleration of thigh data, captured users operate the robotic assistive prosthetic device 402 using the various tuning settings at the various speeds. In other examples, one or more external sensors (not shown) may be configured to capture one or more of these types of biomechanical data.

Generally speaking, the robotic assistive prosthetic computing device 404 may include one or more processors 410 and a memory 412 (e.g., volatile memory, non-volatile memory), as well as a controller 414 configured to generate and send control signals to the robotic assistive prosthetic device 402, e.g., to modify the tuning settings associated with the robotic assistive prosthetic device 402. The memory 412 may be accessible by the one or more processors 410 (e.g., via a memory controller). The one or more processors 410 may interact with the memory 412 to obtain, for example, computer-readable instructions stored in the memory 412. The computer-readable instructions stored in the memory 412 may cause the one or more processors 410 to execute one or more applications, including a robotic assistive prosthetic tuning application 416. Executing the robotic assistive prosthetic tuning application 416 may include, for instance, receiving biomechanical sensor data captured by the sensors 403 or by one or more external sensors, and sending the received biomechanical sensor data to the robotic assistive prosthetic user preference prediction computing device 406 and/or otherwise to be stored in a robotic assistive prosthetic biomechanical database 425.

Moreover, executing the robotic assistive prosthetic tuning application 416 may include receiving indications of predicted robotic assistive prosthetic user preferences from the robotic assistive prosthetic user preference prediction computing device 406, and causing the controller 414 to generate and send control signals to the robotic assistive prosthetic device 402, e.g., to modify the tuning settings associated with the robotic assistive prosthetic device based on the predicted robotic assistive prosthetic user preferences from the robotic assistive prosthetic user preference prediction computing device 406. Furthermore, the computer-readable instructions stored on the memory 412 may include instructions for carrying out any of the steps of the method 600, described in greater detail below with respect to FIG. 6, below.

Generally speaking, the robotic assistive prosthetic user preference prediction computing device 406 may include one or more processors 418 and a memory 420 (e.g., volatile memory, non-volatile memory) accessible by the one or more processors 418 (e.g., via a memory controller). The one or more processors 418 may interact with the memory 420 to obtain, for example, computer-readable instructions stored in the memory 420. The computer-readable instructions stored in the memory 420 may cause the one or more processors to execute one or more applications, including a robotic assistive prosthetic model training application 422, a robotic assistive prosthetic tuning preference model 428, and/or a robotic assistive prosthetic predictor application 430.

Figure 5:
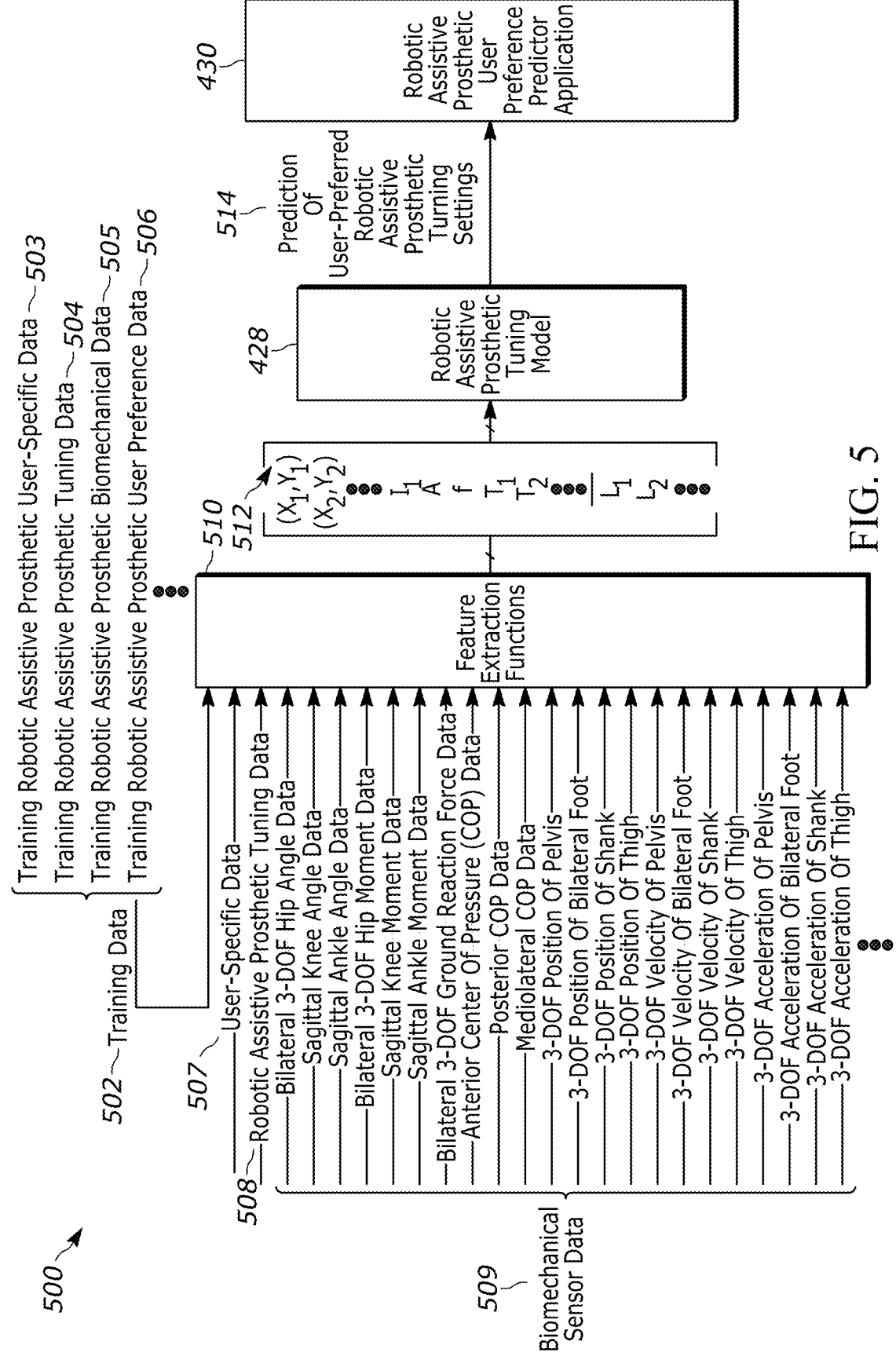
FIG. 5 illustrates a block diagram of an example machine learning model for predicting user preferences with respect to robotic assistive prostheses, in accordance with some embodiments.

Executing the robotic assistive prosthetic model training application 414 may include obtaining various training datasets, which may be stored in various databases, including, for instance, a robotic assistive prosthetic user database 423, which may store user-specific data for new or historical users, a robotic assistive prosthetic tuning database 424, which may store robotic assistive prosthetic tuning data for new or historical users, a robotic assistive prosthetic biomechanical database 425, which may store biomechanical data captured while new or historical users operate the robotic assistive prosthetic devices using the various tuning settings at various speeds, and a user preference database 426, which may store user preference data provided by new users or historical users based on operating the robotic assistive prosthetic devices using the various tuning settings at various speeds, in order to train a robotic assistive prosthetic user preference model 416 in accordance with the scheme 500 discussed below with respect to FIG. 5.

Now referring to FIG. 5, the robotic assistive prosthetic user preference model training application 422 may train the robotic assistive prosthetic user preference model 428 in accordance with the scheme 500, and the robotic assistive prosthetic user preference predictor application 430 may operate the trained model 428 in accordance with the scheme 500.

The robotic assistive prosthetic user preference model training application 422 can receive various input signals, including training data 502 for a plurality of historical users using robotic assistive prostheses, including, for instance, user-specific data 503 for historical users, robotic assistive prosthetic tuning data 504 for historical users, robotic assistive prosthetic biomechanical data 505 captured while the historical users operated the robotic assistive prosthetic devices using the various tuning settings at various speeds, and user preference data 506 provided by the historical users based on operating the robotic assistive prosthetic devices using the various tuning settings at various speeds. The robotic assistive user preference model training application

422 can also receive new data (i.e., data relating to users and their use of robotic prosthetic devices, for whom preferences are to be predicted). For instance, the new data may include new user-specific data 507 for a new user, new robotic assistive prosthetic tuning data 508 for the new user's use of the robotic assistive prosthetic device, and robotic assistive prosthetic biomechanical data 509 captured while the new user operates the robotic assistive prosthetic device using the various tuning settings at various speeds.

For instance, the historical (503) and new (507) user-specific data may include data related to the user physiologically, such as the historical and/or new user's height, weight, age, gender, etc. The historical (504) and new (508) prosthetic tuning data may include data related to the tuning settings associated with the robotic assistive prosthetic device as operated by the user or users. For instance, the user may operate the robotic assistive prosthetic device using various tuning settings, such as ankle stiffness settings (e.g., several ankle stiffness settings ranging from less stiff to more stiff, which may be recorded as a percentage deviation from user's preferred prosthesis ankle stiffness) at various speeds (e.g., on a treadmill with several speed settings), all of which may be included in the historical (504) and new (508) prosthetic tuning data. The historical (505) and new (509) robotic assistive prosthetic biomechanical data may include any of: bilateral three degree-of-freedom (3-DOF) hip angle data, sagittal knee angle data, sagittal ankle angle data, bilateral 3-DOF hip moment data, sagittal knee moment data, and sagittal ankle moment data, bilateral 3-DOF ground reaction force, anterior center of pressure (COP) data, posterior COP data, mediolateral COP data, 3-DOF position of pelvis data, 3-DOF position of bilateral foot data, 3-DOF position of shank data, 3-DOF position of thigh data, 3-DOF velocity of pelvis data, 3-DOF velocity of bilateral foot data, 3-DOF velocity of shank data, 3-DOF velocity of thigh data, 3-DOF acceleration of pelvis data, 3-DOF acceleration of bilateral foot data, 3-DOF acceleration of shank data, or 3-DOF acceleration of thigh data, captured while the historical and/or new users operate the robotic assistive prosthetic device using the various tuning settings at the various speeds discussed with respect to the historical (504) and new (508) prosthetic tuning data. Finally, the training robotic assistive prosthetic user preference data 506 may include data indicative of the historical users' preferred tuning settings (e.g., at each of the various speeds, or overall). For instance, in some examples, the training robotic assistive prosthetic user preference data 506 may include an indication of each historical user's rating of each tuning setting at each speed, or an indication of each historical user's overall preferred tuning setting.

Generally speaking, in some cases, such as for classical ML algorithms (KNN and SVR), feature extraction functions 510 can operate on at least some of these input signals to generate feature vectors, or logical groupings of parameters associated with user-preferred robotic assistive prosthetic turning settings. These results can be used as a set of labels for the feature vectors. Accordingly, the feature extraction functions 510 can generate feature vectors 512 using the training data 502. However, in other cases, such as when using deep learning algorithms (e.g., ANN, CNN, LSTM), the training data 502 may be used to train the machine learning model 428 without any feature extraction functions 510 or feature vectors 512.

In any case, the training application 422 can train the machine learning model 428 using supervised learning, unsupervised learning, reinforcement learning, or any other suitable technique, as discussed in greater detail above.

Moreover, the training application 422 can train the machine learning model 428 as a standard regression model.

Over time, as the training application 422 trains the machine learning model 428, the trained machine learning model 428 may learn to predict user-preferred robotic assistive prosthetic tuning settings for a new user based on the new user-specific data 507, robotic assistive prosthetic tuning data 508, and robotic assistive prosthetic biomechanical data 509 for that user. For instance, the robotic assistive prosthetic user preference predictor application 430 may receive new user-specific data 507, robotic assistive prosthetic tuning data 508, and robotic assistive prosthetic biomechanical data 509 for a new user as inputs (e.g., via the computing device 404 or 406), and may apply the trained machine learning model 428 to the new user-specific data 507, robotic assistive prosthetic tuning data 508, and robotic assistive prosthetic biomechanical data 509 for the new user. The trained machine learning model 428 may then generate predicted user-preferred robotic prosthetic tuning settings for the new user using the new user-specific data 507, robotic assistive prosthetic tuning data 508, and robotic assistive prosthetic biomechanical data 509 for the new user, and may send an indication of the predicted user-preferred robotic prosthetic tuning settings to the robotic assistive prosthetic computing device 404, which may use the predicted user-preferred robotic prosthetic tuning settings to generate control signals to control the robotic assistive prosthetic device 402, e.g., via the controller 414, to modify the tuning settings of the robotic assistive prosthetic device 402 to match the user-preferred robotic prosthetic tuning settings.

Furthermore, in some examples, the computer-readable instructions stored on the memory 420 may include instructions for carrying out any of the steps of the method 600, described in greater detail below with respect to FIG. 6.

Example Method

FIG. 6 illustrates a flow diagram of an example method 600 for using machine learning methods to predict user preferences with respect to robotic assistive prostheses and custom tune the robotic assistive prostheses for individual users based on the predicted user preferences, in accordance with some embodiments. One or more steps of the method 600 may be implemented as a set of instructions stored on a computer-readable memory (e.g., memories 412 and/or 420) and executable on one or more processors (e.g., processors 410 and/or 418).

At block 602, a training biomechanical dataset, including historical biomechanical sensor data for a plurality of users operating a robotic assistive prosthetic device using a plurality of tuning settings at a plurality of speeds, may be generated. For instance, the plurality of tuning settings may include a plurality of ankle stiffness tuning settings for the robotic assistive prosthetic device. The plurality of speeds may include a plurality of speeds as each user walks or runs using the robotic assistive prosthetic device (e.g., on a treadmill). In some examples, at least a portion of the historical biomechanical sensor data may be captured by onboard sensors on the robotic assistive prosthetic device itself. Moreover, in some examples, at least a portion of the historical biomechanical sensor data may be captured by external sensors. The historical biomechanical sensor data may include data for each individual stride.

The historical biomechanical sensor data may include one or more of: bilateral three degree-of-freedom (3-DOF) hip angle data, sagittal knee angle data, sagittal ankle angle data, bilateral 3-DOF hip moment data, sagittal knee moment data, and sagittal ankle moment data, bilateral 3-DOF ground reaction force, anterior center of pressure (COP) data, posterior COP data, mediolateral COP data, 3-DOF position of pelvis data, 3-DOF position of bilateral foot data, 3-DOF position of shank data, 3-DOF position of thigh data, 3-DOF velocity of pelvis data, 3-DOF velocity of bilateral foot data, 3-DOF velocity of shank data, 3-DOF velocity of thigh data, 3-DOF acceleration of pelvis data, 3-DOF acceleration of bilateral foot data, 3-DOF acceleration of shank data, or 3-DOF acceleration of thigh data, for a plurality of historical users, operating the robotic assistive prosthetic device using a plurality of robotic prosthetic assistive device settings, at a plurality of speeds.

At block 604, a training user preference dataset including historical user tuning preference data for the plurality of users for each respective tuning setting and speed of the robotic assistive prosthetic device may be generated. The user tuning preference data may include user ratings of comfort levels at each respective tuning setting and speed, and/or user indications of a preferred tuning setting at each speed.

In some examples, blocks 602 and 604 may be combined as one step, with a single training dataset including historical biomechanical sensor data for a plurality of users operating a robotic assistive prosthetic device using a plurality of tuning settings at a plurality of speeds, as samples, and including historical user tuning preference data for the plurality of users for each respective tuning setting and speed of the robotic assistive prosthetic device, as labels. At block 606, a robotic assistive prosthetic device tuning preference machine learning model may be trained, using the training biomechanical dataset and the training user preference dataset, to predict user tuning preferences for the robotic assistive prosthetic device based on biomechanical sensor data for the robotic assistive prosthetic device associated with a user.

At block 608, new biomechanical sensor data, associated with a particular user, for the robotic assistive prosthetic device operating using the plurality of tuning settings at the plurality of speeds may be obtained. For instance, the plurality of tuning settings may include a plurality of ankle stiffness tuning settings for the robotic assistive prosthetic device. The plurality of speeds may include a plurality of speeds the user walks or runs using the robotic assistive prosthetic device (e.g., on a treadmill). In some examples, at least a portion of the new biomechanical sensor data may be captured by onboard sensors on the robotic assistive prosthetic device itself. Moreover, in some examples, at least a portion of the new biomechanical sensor data may be captured by external sensors. The new biomechanical sensor data may include data for each individual stride.

The new biomechanical sensor data may include one or more of: bilateral three degree-of-freedom (3-DOF) hip angle data, sagittal knee angle data, sagittal ankle angle data, bilateral 3-DOF hip moment data, sagittal knee moment data, and sagittal ankle moment data, bilateral 3-DOF ground reaction force, anterior center of pressure (COP) data, posterior COP data, mediolateral COP data, 3-DOF position of pelvis data, 3-DOF position of bilateral foot data, 3-DOF position of shank data, 3-DOF position of thigh data, 3-DOF velocity of pelvis data, 3-DOF velocity of bilateral foot data, 3-DOF velocity of shank data, 3-DOF velocity of thigh data, 3-DOF acceleration of pelvis data, 3-DOF acceleration of bilateral foot data, 3-DOF acceleration of shank data, or 3-DOF acceleration of thigh data, for the particular user, operating the robotic assistive prosthetic device using a plurality of robotic prosthetic assistive device settings, at a plurality of speeds.

At block 610, the trained robotic assistive prosthetic device tuning preference machine learning model may be applied to the new biomechanical sensor data associated with the particular user to predict user tuning preference data for the robotic assistive prosthetic device. For instance, the trained robotic assistive prosthetic device tuning preference machine learning model may receive the new biomechanical sensor data associated with the particular user as an input, and may output predicted user tuning preference data, which may include may include predicted comfort levels for the particular user at each respective tuning setting (e.g., at each ankle stiffness setting) and speed, and/or a predicted preferred tuning setting (e.g., a predicted preferred ankle stiffness setting) for the user at each speed.

At block 612, one or more tuning settings for the robotic assistive prosthetic device may be modified based on the predicted user tuning preference data. For instance, an ankle stiffness setting for the robotic assistive prosthetic may be modified based on the predicted preferences for the particular user. In some examples, the ankle stiffness setting may be generally modified to be more or less stiff based on the predicted user preferences, while in some examples, the ankle stiffness setting for the robotic assistive prosthetic may be modified such that the ankle stiffness for the robotic assistive prosthetic changes based on the predicted user preferences and on a determined speed or activity level of the user operating the robotic assistive prosthetic.

Additional Considerations

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter of the present disclosure.

Additionally, certain embodiments are described herein as including logic or a number of components, modules, or mechanisms. Modules may constitute either software modules (e.g., code stored on a machine-readable medium) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

A hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module in dedicated and permanently configured circuitry or in temporarily configured circuitry (e.g., configured by software) may be driven by cost and time considerations.

Accordingly, the term hardware should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware and software modules can provide information to, and receive information from, other hardware and/or software modules. Accordingly, the described hardware modules may be regarded as being communicatively coupled. Where multiple of such hardware or software modules exist contemporaneously, communications may be achieved through signal transmission (e.g., over appropriate circuits and buses) that connect the hardware or software modules. In embodiments in which multiple hardware modules or software are configured or instantiated at different times, communications between such hardware or software modules may be achieved, for example, through the storage and retrieval of information in memory structures to which the multiple hardware or software modules have access. For example, one hardware or software module may perform an operation and store the output of that operation in a memory device to which it is communicatively coupled. A further hardware or software module may then, at a later time, access the memory device to retrieve and process the stored output. Hardware and software modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as an SaaS. For example, as indicated above, at least some of the operations may be performed by a group of computers (as examples of machines including processors), these operations being accessible via a network (e.g., the Internet) and via one or more appropriate interfaces (e.g., APIs).

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" or a "routine" is a self-consistent sequence of operations or similar processing leading to a desired result. In this context, algorithms, routines and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Upon reading this disclosure, those of skill in the art will appreciate still additional alternative structural and functional designs for preserving privacy during a navigation session through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented method, comprising:

generating, by one or more processors of a system including a robotic assistive device, a training biomechanical dataset, including historical biomechanical sensor data for a plurality of users operating the robotic assistive device using a plurality of tuning settings at a plurality of speeds;

generating, by the one or more processors, a training user preference dataset including historical user tuning preference data for the plurality of users for each respective tuning setting and speed of the robotic assistive device;

training, by the one or more processors, using the training biomechanical dataset and the training user preference dataset, a robotic assistive device tuning preference machine learning model to predict user tuning preferences for the robotic assistive device based on biomechanical sensor data for the robotic assistive device associated with a user;

obtaining, by the one or more processors, new biomechanical sensor data, associated with a particular user, for the robotic assistive device operating using the plurality of tuning settings at the plurality of speeds;

applying, by the one or more processors, the trained robotic assistive device tuning preference machine learning model to the new biomechanical sensor data associated with the particular user to predict user tuning preference data for the robotic assistive device; and automatically modifying, by the one or more processors, one or more tuning settings for the robotic assistive prosthetic device based on the predicted user tuning preference data, wherein automatically modifying the one or more tuning settings for the robotic assistive device includes causing a motor to adjust one or more mechanical properties of the robotic assistive device.

2. The computer-implemented method of claim 1, wherein at least a portion of the new biomechanical sensor data is captured by onboard sensors of the robotic assistive device.

3. The computer-implemented method of claim 1, wherein at least a portion of the historical biomechanical sensor data is captured by onboard sensors of the robotic assistive device.

4. The computer-implemented method of claim 1, wherein the new biomechanical sensor data and the historical biomechanical sensor data each include one or more of: bilateral three degree-of-freedom (3-DOF) hip angle data, sagittal knee angle data, sagittal ankle angle data, bilateral 3-DOF hip moment data, sagittal knee moment data, and sagittal ankle moment data, bilateral 3-DOF ground reaction force, anterior center of pressure (COP) data, posterior COP data, mediolateral COP data, 3-DOF position of pelvis data, 3-DOF position of bilateral foot data, 3-DOF position of shank data, 3-DOF position of thigh data, 3-DOF velocity of pelvis data, 3-DOF velocity of bilateral foot data, 3-DOF velocity of shank data, 3-DOF velocity of thigh data, 3-DOF acceleration of pelvis data, 3-DOF acceleration of bilateral foot data, 3-DOF acceleration of shank data, or 3-DOF acceleration of thigh data.

5. The computer-implemented method of claim 1, wherein new biomechanical sensor data and historical sensor data are captured for each stride of the robotic assistive device.

6. A system comprising:

a robotic assistive device;

one or more processors; and a non-transitory memory storing computer-readable instructions that, when executed by the one or more processors, cause the one or more processors to:

generate a training biomechanical dataset, including historical biomechanical sensor data for a plurality of users operating the robotic assistive device using a plurality of tuning settings at a plurality of speeds;

generate a training user preference dataset including historical user tuning preference data for the plurality of users for each respective tuning setting and speed of the robotic assistive device;

train, using the training biomechanical dataset and the training user preference dataset, a robotic assistive device tuning preference machine learning model to predict user tuning preferences for the robotic assistive device based on biomechanical sensor data for the robotic assistive device associated with a user;

obtain new biomechanical sensor data, associated with a particular user, for the robotic assistive device operating using the plurality of tuning settings at the plurality of speeds;

apply the trained robotic assistive device tuning preference machine learning model to the new biomechanical sensor data associated with the particular user to predict user tuning preference data for the robotic assistive device; and automatically modify one or more tuning settings for the robotic assistive device based on the predicted user tuning preference data, wherein automatically modifying the one or more tuning settings for the robotic assistive device includes causing a motor to adjust one or more mechanical properties of the robotic assistive device.

7. The system of claim 6, wherein the robotic assistive device includes one or more onboard sensors configured to capture at least a portion of the new biomechanical sensor data.

8. The system of claim 6, wherein the robotic assistive device includes one or more onboard sensors configured to capture at least a portion of the historical biomechanical sensor data.

9. The system of claim 6, wherein the new biomechanical sensor data and the historical biomechanical sensor data each include one or more of: bilateral three degree-of-freedom (3-DOF) hip angle data, sagittal knee angle data, sagittal ankle angle data, bilateral 3-DOF hip moment data, sagittal knee moment data, and sagittal ankle moment data, bilateral 3-DOF ground reaction force, anterior center of pressure (COP) data, posterior COP data, mediolateral COP data, 3-DOF position of pelvis data, 3-DOF position of bilateral foot data, 3-DOF position of shank data, 3-DOF position of thigh data, 3-DOF velocity of pelvis data, 3-DOF velocity of bilateral foot data, 3-DOF velocity of shank data, 3-DOF velocity of thigh data, 3-DOF acceleration of pelvis data, 3-DOF acceleration of bilateral foot data, 3-DOF acceleration of shank data, or 3-DOF acceleration of thigh data.

10. The system of claim 6, wherein new biomechanical sensor data and historical sensor data are captured for each stride of the robotic assistive prosthetic device.

11. A non-transitory computer-readable medium storing instructions that, when executed by one or more processors of a system including a robotic assistive device, cause the one or more processors to:

generate a training biomechanical dataset, including historical biomechanical sensor data for a plurality of users operating the robotic assistive device using a plurality of tuning settings at a plurality of speeds;

generate a training user preference dataset including historical user tuning preference data for the plurality of users for each respective tuning setting and speed of the robotic assistive device;

train, using the training biomechanical dataset and the training user preference dataset, a robotic assistive device tuning preference machine learning model to predict user tuning preferences for the robotic assistive device based on biomechanical sensor data for the robotic assistive device associated with a user;

obtain new biomechanical sensor data, associated with a particular user, for the robotic assistive device operating using the plurality of tuning settings at the plurality of speeds;

apply the trained robotic assistive device tuning preference machine learning model to the new biomechanical sensor data associated with the particular user to predict user tuning preference data for the robotic assistive device; and automatically modify one or more tuning settings for the robotic assistive device based on the predicted user tuning preference data, wherein automatically modifying the one or more tuning settings for the robotic assistive device includes causing a motor to adjust one or more mechanical properties of the robotic assistive device.

12. The non-transitory computer-readable medium of claim 11, wherein at least a portion of the new biomechanical sensor data is captured by onboard sensors of the robotic assistive device.

13. The non-transitory computer-readable medium of claim 11, wherein at least a portion of the historical biomechanical sensor data is captured by onboard sensors of the robotic assistive device.

14. The non-transitory computer-readable medium of claim 11, wherein the new biomechanical sensor data and the historical biomechanical sensor data each include one or more of: bilateral three degree-of-freedom (3-DOF) hip angle data, sagittal knee angle data, sagittal ankle angle data, bilateral 3-DOF hip moment data, sagittal knee moment data, and sagittal ankle moment data, bilateral 3-DOF ground reaction force, anterior center of pressure (COP) data, posterior COP data, mediolateral COP data, 3-DOF position of pelvis data, 3-DOF position of bilateral foot data, 3-DOF position of shank data, 3-DOF position of thigh data, 3-DOF velocity of pelvis data, 3-DOF velocity of bilateral foot data, 3-DOF velocity of shank data, 3-DOF velocity of thigh data, 3-DOF acceleration of pelvis data, 3-DOF acceleration of bilateral foot data, 3-DOF acceleration of shank data, or 3-DOF acceleration of thigh data.

* * * * *